United States Patent
Weser et al.

(10) Patent No.: US 12,220,470 B2
(45) Date of Patent: Feb. 11, 2025

(54) PIGMENT SUSPENSION AND COSMETIC AGENT PREPARED USING THE PIGMENT SUSPENSION

(71) Applicant: Henkel AG & Co. KGaA, Duesseldorf (DE)

(72) Inventors: Gabriele Weser, Essen (DE); Ulrike Schumacher, Duesseldorf (DE); Claudia Kolonko, Remscheid (DE); Caroline Kriener, Duesseldorf (DE); Jing Hodes, Hagen (DE); Irmgard Bender, Duesseldorf (DE); Phillip Jaiser, Langenfeld (DE); Marc Nowottny, Moenchengladbach (DE); Juergen Schoepgens, Schwalmtal (DE); Torsten Lechner, Langenfeld (DE); Andreas Walter, Ratingen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 86 days.

(21) Appl. No.: 18/005,808

(22) PCT Filed: May 27, 2021

(86) PCT No.: PCT/EP2021/064185
§ 371 (c)(1),
(2) Date: Jan. 17, 2023

(87) PCT Pub. No.: WO2022/012807
PCT Pub. Date: Jan. 20, 2022

(65) Prior Publication Data
US 2023/0285252 A1   Sep. 14, 2023

(30) Foreign Application Priority Data

Jul. 17, 2020   (DE) .......................... 102020208953.1

(51) Int. Cl.
| | | |
|---|---|---|
| *A61Q 5/10* | (2006.01) | |
| *A61K 8/19* | (2006.01) | |
| *A61K 8/55* | (2006.01) | |
| *A61K 8/58* | (2006.01) | |
| *A61Q 5/06* | (2006.01) | |

(52) U.S. Cl.
CPC .................. *A61K 8/19* (2013.01); *A61K 8/55* (2013.01); *A61K 8/585* (2013.01); *A61Q 5/065* (2013.01); *A61K 2800/412* (2013.01); *A61K 2800/43* (2013.01)

(58) Field of Classification Search
CPC . A61K 8/19; A61K 8/55; A61K 8/585; A61K 2800/412; A61K 2800/43; A61K 8/86; A61K 8/044; A61Q 5/065
USPC ............................................................. 8/405
See application file for complete search history.

(56) References Cited

U.S. PATENT DOCUMENTS

2010/0083446 A1 * 4/2010 Brun ...................... A61K 8/891
                                                                8/405
2014/0298594 A1   10/2014 Weser et al.

FOREIGN PATENT DOCUMENTS

| CN | 103476387 A * | 12/2013 | ............... A61K 8/31 |
|---|---|---|---|
| DE | 102018213814 A1 | 2/2020 | |
| WO | WO2011024300 A1 * | 3/2011 | ............... A61Q 5/10 |
| WO | 2020035187 A1 | 2/2020 | |
| WO | 2021018446 A1 | 2/2021 | |
| WO | 2021104703 A1 | 6/2021 | |

* cited by examiner

*Primary Examiner* — Eisa B Elhilo
(74) *Attorney, Agent, or Firm* — Lorenz & Kopf, LLP

(57) ABSTRACT

A pigment suspension, a cometic agent obtainable from a pigment suspension, and a kit-of-parts containing a pigment suspension are provided. A pigment suspension includes (a) at least one coloring compound selected from the group consisting of pigments, (b) at least one phosphoric ester, and (c) water.

14 Claims, No Drawings

PIGMENT SUSPENSION AND COSMETIC AGENT PREPARED USING THE PIGMENT SUSPENSION

CROSS-REFERENCE TO RELATED APPLICATION

This application is a U.S. National-Stage entry under 35 U.S.C. § 371 based on International Application No. PCT/EP2021/064185, filed May 27, 2021, which was published under PCT Article 21(2) and which claims priority to German Application No. 102020208953.1, filed Jul. 17, 2020, which are all hereby incorporated in their entirety by reference.

TECHNICAL FIELD

The subject of the present application is a pigment suspension comprising a pigment, a dispersant, and a carrier medium. Another article is a cosmetic agent prepared using the pigment suspension and an organosilicon compound.

Pigments are frequently used in coatings, paints, printing inks, powder coatings, cosmetics, or plastics for coloration. Paints, varnishes, printing inks, cosmetics and powder coatings are liquid or powder coating materials that are applied to surfaces to obtain both improved or altered optical and physical properties.

BACKGROUND

The change in shape and color of keratin fibers, especially hair, is a key area of modern cosmetics. To change the hair color, the expert knows various coloring systems depending on coloring requirements. Oxidation dyes are usually used for permanent, intensive dyeing with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are characterized by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyes with direct colorings usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed without residue by a few washes with surfactant-comprising cleaning agents. Various products of this type are available on the market under the name hair mascara.

For applications in the cosmetic field, for example in the color modification of keratinic fibers with pigments, it is important that the pigments are provided to the user in a storage-stable and dosage-capable form. This can be done in the form of a storage-stable pigment suspension.

Ground pigment powders and water are usually used to produce inorganic pigment suspensions. If necessary, organic, or inorganic dispersing aids must be added in small quantities.

Some pigments, especially iron oxide-based pigments, have a strong tendency to form so-called agglomerates. This means that the individual primary particles adhere strongly to each other and must therefore be broken up with high shear forces to distribute the pigments evenly in the carrier medium. To prevent undesired agglomeration after the shear energy has been removed, the dispersant forms a protective shell around everyone, dispersed pigment particle. A distinction is made between steric and electrostatic stabilization by the dispersant.

BRIEF SUMMARY

A pigment suspension, a cometic agent obtainable from a pigment suspension, and a kit-of-parts containing a pigment suspension are provided. A pigment suspension includes (a) at least one coloring compound selected from the group consisting of pigments, (b) at least one phosphoric ester, and (c) water.

A cosmetic agent is obtainable by combining a pigment suspension comprising (a) at least one coloring compound selected from the group consisting of pigments, (b) at least one phosphoric ester, and (c) water, with one or more organic $C_1$-$C_6$ alkoxysilanes and/or condensation products thereof.

A kit-of-parts for dyeing keratinous material includes, separately packaged, a first container including an agent (a') including (a1) at least one or more organic $C_1$-$C_6$-alkoxysilanes, and a second container comprising an agent (a") including (a2) a pigment suspension including (a) at least one coloring compound selected from the group consisting of pigments, (b) at least one phosphoric ester, and (c) water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

With respect to the dispersant, it is not only desirable that it can protect from agglomeration a wide variety of pigments which differ, for example, in composition, particle size, particle shape and/or surface post-treatment, but also that it allows the pigment suspension to be used in cosmetic agents.

It is an object of the present disclosure to provide pigment suspensions which are also suitable for use in cosmetic agents, which can be prepared simply and inexpensively, and which are stable in storage. In particular, the pigments in the pigment suspension should be stable against agglomeration.

It has been shown that pigment suspensions comprising at least one phosphoric acid ester as dispersant meet these requirements.

Accordingly, a first subject matter of the application is a pigment suspension comprising a) at least one coloring compound selected from the group of pigments, b) at least one phosphoric acid ester, and c) water.

As the first ingredient essential to the present disclosure, the pigment suspensions contain at least one colorant compound from the group of pigments.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A beaker glass is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable pigments can be of inorganic and/or organic origin.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

Colored pearlescent pigments are also particularly preferred colorants from the group of pigments as contemplated herein. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

Also preferred mica-based pigments are synthetically produced mica platelets coated with metal oxide, based on synthetic fluorophlogopite (INCI. Synthetic Fluorphlogopite). The synthetic fluorophlogopite platelets are coated, for example, with tin oxide, iron oxide(s) and/or titanium dioxide. The metal oxide layers can also have pigments such as iron hexacyanidoferrate(II/III) or carmine red In a preferred embodiment, a pigment suspension comprises at least one coloring compound selected from the group of inorganic pigments, black iron oxide (CI 77499), yellow iron oxide (CI 77492), red iron oxide (CI 77491) and mixtures thereof.

Yellow iron oxide (or iron oxide yellow) is the name for FeO(OH), in the color index under C.I. Pigment Yellow 42 listed.

Red iron oxide (or iron oxide red) is the name for $Fe_2O_3$, in the color index under C.I. Pigment Red 101 listed. Depending on the particle size, red iron oxide pigments can be adjusted to be very yellowish (small particle size) to very blueish (coarse particles).

Black iron oxide (or iron oxide black) is listed in the Color Index under C.I. Pigment Black 11 listed. Iron oxide black is ferromagnetic. The chemical formula is often given as $Fe_3O_4$, there is a solid solution of $Fe_2O_3$ and FeO with inverse spinel structure. Further black pigments are obtained by doping with chromium, copper, or manganese.

Brown, Black Iron Oxide (or Iron Oxide Brown) usually does not refer to a defined pigment, but to a mixture of yellow, red and/or black iron oxide.

Surprisingly, it has been shown that iron oxide pigments with particle diameters in the range of 100 to 1,000 nm, more preferably 150 nm 700 nm, can be stably dispersed and show no or little agglomeration.

Iron oxide pigments usually have particle diameters in the range of 2,000 to 4,000 nm. For some applications, especially for cosmetic purposes, it may be advantageous to use iron oxide pigments with significantly smaller particle diameters. For example, hair dyes with iron oxide pigments that have a particle diameter in the range of 100 to 1,000 nm, more preferably 150 nm 700 nm, show better durability and better gray coverage.

Accordingly, a pigment suspension is preferred in which the coloring compound comprises a pigment from the group of iron oxide pigments.

Even more preferred is a pigment suspension in which the coloring compound comprises a pigment from the group of iron oxide pigments, wherein the iron oxide pigments have a particle diameter in the range of 100 to 1,000 nm, more preferably 150 nm 700 nm.

The same is true for organic pigments. These usually have particle diameters in the range of 2,000 to 3,000 nm. With the aid of at least one Phosphoric acid ester, organic pigments with a particle diameter in the range from 100 to 1,000 nm, more preferably 150 nm 700 nm, can be stably dispersed in aqueous pigment suspensions.

Accordingly, a pigment suspension is preferred in which the coloring compound comprises a pigment from the group of organic pigments.

Even more preferred is a pigment suspension in which the coloring compound comprises at least one pigment selected from the group of organic pigments, wherein the organic pigment has a particle diameter in the range of 100 to 1,000 nm, more preferably 150 nm 700 nm.

The particle diameter of the pigments, in particular the iron oxide pigments and/or the organic pigments, can be determined, for example, by laser light scattering methods and laser light diffraction methods.

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketopyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In certain preferred pigment suspensions, the coloring compound comprises at least one organic pigment selected from the group of carmine, quinacridone, phthalocyanine, Sorgho, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with the color index numbers CI 61565, CI 61570, CI 74260, orange pigments with the color index numbers CI 11725, CI 15510, CI 45370, CI 71105, red pigments with the color index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

In addition to the above-mentioned, particularly preferred pigments from the group of inorganic and organic pigments, the pigment suspension may contain further pigments. These further pigments may comprise effect pigments comprising pigments with substrate platelets made of metal and/or pigments with substrate platelets made of a metal alloy. Preferably, however, the pigment suspension comprises less than 0.05 wt. %, based on the total pigment suspension, of effect pigments comprising pigments with substrate platelets of metal and/or pigments with substrate platelets of a metal alloy. More preferably, the pigment suspension does not contain effect pigments comprising pigments with substrate platelets of metal and/or pigments with substrate platelets of a metal alloy.

In addition to pigments, other coloring compounds may be included in the pigment suspension. The further coloring compounds may comprise direct dyes.

The amount of pigment in the pigment suspension depends in particular on the type of pigment(s) and its intended use. Preferably, the amount of pigment is between 0.5 and 70 wt. %, more preferably between 1 and 60 wt. % and most preferably between 5 and 50 wt. %, in each case based on the total weight of the pigment suspension.

Examples of particularly suitable inorganic pigments are commercially available, for example, under the trade names Rona®, Colorona®, Xirona®, Dichrona® and Timiron® from the company Merck, Ariabel® and Unipure® from the company Sensient, Prestige® from the company Eckart Cosmetic Colors and Sunshine® from the company Sunstar.

Very particularly preferred pigments with the trade name Colorona® are, for example:
Colorona Copper, Merck, MICA, CI 77491 (IRON OXIDES)
Colorona Copper Fine, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, MICA, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)
Colorona SynCopper, Merck, Synthetic Fluorphlogopite (and) Iron Oxides
Colorona SynBronze, Merck, Synthetic Fluorphlogopite (and) Iron Oxides Further particularly preferred pigments with the trade name Xirona® are, for example:
Xirona® Golden Sky, Merck, Silica, CI 77891 (Titanium Dioxide), Tin Oxide
Xirona® Caribbean Blue, Merck, Mica, CI 77891 (Titanium Dioxide), Silica, Tin Oxide
Xirona® Kiwi Rose, Merck, Silica, CI 77891 (Titanium Dioxide), Tin Oxide
Xirona® Magic Mauve, Merck, Silica, CI 77891 (Titanium Dioxide), Tin Oxide
Xirona® Le Rouge, Merck, Iron Oxides (and) Silica In addition, particularly preferred pigments with the trade name Unipure® are, for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica Also particularly preferred pigments with the trade name Flamenco® are, for example:
- Flamenco® Summit Turquoise T30D, BASF, Titanium Dioxide (and) Mica
- Flamenco® Super Violet 530Z, BASF, Mica (and) Titanium Dioxide As a second ingredient essential to the present disclosure, the pigment suspension comprises at least one phosphoric acid ester.

Phosphoric acid esters are esters of orthophosphoric acid, which are formally or formed by the reaction of the acid and alcohols with elimination of water. A distinction is made between monoesters, diesters and triesters. Monoesters are formed by the reaction of the alcohol with polyphosphoric acid, while mixtures of monoesters and diesters are prepared by reacting the alcohol with phosphorus pentoxide.

The esters of orthophosphoric acid with aliphatic alcohols can be used as phosphoric acid esters. The aliphatic alcohols are linear or branched, saturated or unsaturated alcohols with 1 to 22 carbon atoms and 0, 1, 2 or 3 double bonds. Typical representatives are, for example, methanol, ethanol n-propanol, isopropanol, n-butanol, sec.-butanol, tert, butanol, n-pentanol, capric alcohol, caprylic alcohol, 2-ethylhexanol, capric alcohol, myristyl alcohol, lauryl alcohol, cetyl alcohol, palmitoleyl alcohol, stearyl alcohol, oleyl alcohol, elaidyl alcohol, petroselyl alcohol, linolyl alcohol, linolenyl alcohol, behenyl alcohol or erucyl alcohol. Preferably, the aliphatic alcohols are branched and saturated alcohols with 11 to 14 carbon atoms. Very preferably, the aliphatic alcohols are a mixture of branched and saturated alcohols with 11 to 14 carbon atoms, which has a high proportion of isotridecanol Accordingly, in a preferred embodiment, the pigment suspension comprises at least one phosphoric acid ester selected from the group of esters of orthophosphoric acid with aliphatic alcohols.

In a particularly preferred embodiment, the pigment suspension comprises at least one phosphoric acid ester comprising an ester of orthophosphoric acid with a branched aliphatic alcohol having 11 to 14 carbon atoms.

A particularly suitable phosphoric acid ester that can be used in the pigment suspension is Phosfetal 218 (CAS number: 154518-38-4, Phosphoric acid, C11-14-isoalkyl esters, C13-rich), which is available from Zschimmer & Schwarz.

Alternatively, the esters of orthophosphoric acid with alkoxylated aliphatic alcohols or the esters of orthophosphoric acid with alkoxylated phenols can be used as phosphoric acid esters. The alkoxylated alcohols are ethoxylated alcohols with 1 to 22 carbon atoms.

In another preferred embodiment, the pigment suspension is exemplified by comprising at least one phosphoric acid ester comprising an ester of orthophosphoric acid with an ethoxylated aliphatic alcohol having from 1 to 22 carbon atoms.

In another particularly preferred embodiment, the pigment suspension comprises at least one phosphoric acid ester comprising an ester of orthophosphoric acid with an ethoxylated aliphatic alcohol having from 8 to 18 carbon atoms.

The average degree of ethoxylation of the aliphatic alcohols is preferably in the range from 2 to 80 and more preferably in the range from 5 to 25.

Another highly preferred phosphoric acid ester that may be included in the pigment suspension as a dispersant is Crodafos SP (INCI: Ceteth-20 phosphates), which is available from Croda.

The alkoxylated phenols are preferably ethoxylated phenols or ethoxylated alkylphenols.

To ensure particularly stable dispersion of the pigments in the pigment suspension, the phosphoric acid ester is preferably used in certain quantity ranges. Thus, it has been found to be particularly advantageous if the pigment suspension comprises—based on the total weight of the pigment suspension—one or more phosphoric acid esters in a total amount of 0.5 to 30 wt. %, preferably 1 to 25 wt. %, more preferably 2 to 20 wt. % and very particularly preferably 5 to 15 wt. %.

In another particularly preferred embodiment, a pigment suspension comprises—based on the total weight of the pigment suspension—one or more phosphoric acid esters comprising an ester of orthophosphoric acid with a branched aliphatic alcohol having from 11 to 14 carbon atoms in a total amount of from 0.5 to 30 wt. %, preferably from 1 to 25 wt. %, more preferably from 2 to 20 wt. % and very particularly preferably from 5 to 15 wt. %.

In another still more preferred embodiment, a pigment suspension comprises—based on the total weight of the pigment suspension—one or more phosphoric acid esters comprising an ester with the INCI designation Ceteth-20 phosphates in a total amount of from 0.5 to 30 wt. %, preferably from 1 to 25 wt. %, more preferably from 2 to 20 wt. % and very particularly preferably from 5 to 15 wt. %.

The third essential component of the pigment suspension is water. The water content is preferably above 20 wt. %, even more preferably above 40 wt. % and particularly preferably above 60 wt. %. In addition to water, the pigment suspension may contain another carrier, for example a $C_1$-$C_4$ alcohol, in particular ethanol or isopropanol. The pigment suspension may additionally contain further organic solvents as carriers, such as methoxybutanol, benzyl alcohol, ethyl diglycol or 1,2-propylene glycol.

The pH value of the pigment suspension is preferably in the alkaline range. Preferably, the pH of the pigment suspension is in the range of 9.5 to 11 and even more preferably in the range of 10 to 10.5.

To adjust the desired pH, the pigment suspension may contain at least one alkalizing agent or at least one acidifying agent. The pH values for the purposes of the present disclosure are pH values measured at a temperature of 22° C.

The present disclosure also relates to a cosmetic composition. This was prepared by combining a pigment suspension according to the present disclosure with one or more organic $C_1$-$C_6$ alkoxysilanes and/or their condensation products. In this way, cosmetic agents can be provided that contain all the desired components beneficial to the cosmetic agent, with the pigments protected from decomposition and the $C_1$-$C_6$ alkoxysilanes protected from hydrolysis.

Such cosmetic agents can be used, for example, in processes for coloring keratinous material, especially human hair.

The exemplary cosmetic agent comprises one or more organic $C_1$-$C_6$ alkoxysilanes and/or their condensation products.

The organic $C_1$-$C_6$ alkoxysilane(s) are organic, non-polymeric silicon compounds, preferably selected from the group of silanes having one, two or three silicon atoms Organic silicon compounds, alternatively called organosilicone compounds, are compounds which either have a direct silicon-carbon bond (Si—C) or in which the carbon is bonded to the silicon atom via an oxygen, nitrogen, or sulfur atom. The organic silicon compounds of the present disclosure are preferably compounds comprising one to three silicon atoms. Organic silicon compounds preferably contain one or two silicon atoms.

According to IUPAC rules, the term silane stands for a group of chemical compounds based on a silicon basic framework and hydrogen. In organic silanes, the hydrogen atoms are completely or partially replaced by organic groups such as (substituted) alkyl groups and/or alkoxy groups.

A characteristic feature of the $C_1$-$C_6$ alkoxysilanes as contemplated herein is that at least one $C_1$-$C_6$ alkoxy group is directly bonded to a silicon atom. The $C_1$-$C_6$ alkoxysilanes as contemplated herein thus comprise at least one structural unit R'R''R'''Si—O—($C_1$-$C_6$ alkyl) where the radicals R', R'' and R''' represent the three-remaining bond valencies of the silicon atom.

The $C_1$-$C_6$ alkoxy group or groups bonded to the silicon atom are very reactive and are hydrolyzed at high rates in the presence of water, the reaction rate depending, among other things, on the number of hydrolysable groups per molecule. If the hydrolysable $C_1$-$C_6$ alkoxy group is an ethoxy group, the organic silicon compound preferably comprises a structural unit R'R''R'''Si—O—$CH_2$—$CH_3$. The radicals R', R'' and R'''again represent the three remaining free valences of the silicon atom.

Even the addition of insignificant amounts of water leads first to hydrolysis and then to a condensation reaction between the organic alkoxysilanes. For this reason, both the organic alkoxysilanes and their condensation products may be present in the cosmetic agent.

A condensation product is understood to be a product formed by the reaction of at least two organic $C_1$-$C_6$ alkoxysilanes with elimination of water and/or with elimination of a $C_1$-$C_6$ alkanol.

The condensation products can, for example, be dimers, or even trimers or oligomers, where in the condensation products are always in balance with the monomers.

Depending on the amount of water used or consumed in the hydrolysis, the equilibrium shifts from monomeric $C_1$-$C_6$ alkoxysilane to condensation product.

In a very particularly preferred embodiment, a cosmetic agent comprises one or more organic $C_1$-$C_6$ alkoxysilanes selected from silanes having one, two or three silicon atoms, the organic silicon compound further comprising one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A very particularly preferred cosmetic agent comprises one or more organic $C_1$-$C_6$ alkoxysilanes selected from the group of silanes having one, two or three silicon atoms, and wherein the $C_1$-$C_6$ alkoxysilanes further comprise one or more basic chemical functions.

Particularly satisfactory results were obtained when $C_1$-$C_6$ alkoxysilanes of the formula (S-I) and/or (S-II) and/or (S-IV) were used in the cosmetic agent. Since, as previously described, hydrolysis/condensation already starts at traces of moisture, the condensation products of the $C_1$-$C_6$ alkoxysilanes of formula (S-I) and/or (S-II) and/or (S-IV) are also included in this embodiment.

In another very particularly preferred embodiment, a cosmetic agent comprises one or more organic $C_1$-$C_6$ alkoxysilanes of the formula (S-I) and/or (S-II),

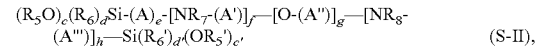

where
R$_1$, R$_2$ independently represent a hydrogen atom or a $C_1$-$C_6$ alkyl group,
L is a linear or branched divalent $C_1$-$C_{20}$ alkylene group,
R$_3$, R$_4$ independently of one another represent a $C_1$-$C_6$ alkyl group,
a, stands for an integer from 1 to 3, and
b stands for the integer 3-a, and

where
R5, R5', R5'', R6, R6' and R6'' independently represent a $C_1$-$C_6$ alkyl group,
A, A', A'', A''' and A'''' independently represent a linear or branched divalent $C_1$-$C_{20}$ alkylene group,
R$_7$ and R$_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III), (A'''')—Si(R$_6$'')$_d$''(OR$_5$'')$_c$''  (S-III), c, stands for an integer from 1 to 3,
d stands for the integer 3-c,
c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
provided that at least one of e, f, g, and h radicals are different from 0, and/or their condensation products.

The substituents R$_1$, R$_2$, R$_3$, R$_4$, R$_5$, R$_5$', R$_5$'', R$_6$, R$_6$', R$_6$'', R$_7$, R$_8$, L, A, A', A'', A''', and A'''' in the compounds of formula (S-I) and (S-II) are explained below as examples: Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—CH($CH_3$)—) and (—$CH_2$—CH($CH_3$)—$CH_2$—).

In the organic silicon compounds of the formula (S-I)

the radicals R$_1$ and R$_2$ independently of one another represent a hydrogen atom or a $C_1$-$C_6$ alkyl group. Most preferably, the radicals R$_1$ and R$_2$ both represent a hydrogen atom.

In the middle part of the organic silicon compound is the structural unit or the linker -L- which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each —L grouping may form—two bonds.

Preferably -L- stands for a linear, bivalent $C_1$-$C_{20}$ alkylene group. Further preferably -L- stands for a linear bivalent $C_1$-$C_6$ alkylene group. Particularly preferred -L stands for a methylene group (CH$_2$—), an ethylene group (—CH$_2$—CH$_2$—), propylene group (—CH$_2$—CH$_2$—CH$_2$—) or butylene (—CH$_2$—CH$_2$—CH$_2$—CH$_2$—). L stands for a propylene group (—CH$_2$—CH$_2$—CH$_2$—)

The alkoxysilanes of the formula (S-I)

$R_1R_2N$-L-Si(OR$_3$)$_a$(R$_4$)$_b$    (S-I), one end of each carries the silicon-comprising group —Si(OR$_3$)$_a$(R$_4$)$_b$.

In the terminal structural unit —Si(OR$_3$)$_a$(R$_4$)$_b$ radicals R3 and R4 independently represent a $C_1$-$C_6$ alkyl group, and particularly preferably $R_3$ and $R_4$ independently represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Cosmetic agents with particularly good coloring properties for keratinous materials could be prepared if the agent comprises at least one organic $C_1$-$C_6$ alkoxysilane of the formula (S-I) in which the radicals $R_3$, $R_4$ independently of one another represent a methyl group or an ethyl group.

Furthermore, colorations with the best wash fastnesses could be obtained if the cosmetic agent comprises at least one organic $C_1$-$C_6$ alkoxysilane of the formula (S-I) in which the radical a represents the number 3. In this case the radial b stands for the number 0.

In another preferred embodiment, a cosmetic agent is wherein it comprises one or more organic $C_1$-$C_6$ alkoxysilanes of the formula (S-I),
where
$R_3$, $R_4$ independently of one another represent a methyl group or an ethyl group and
a stands for the number 3 and
b stands for the number 0.

In another preferred embodiment, a cosmetic agent is wherein it comprises at least one or more organic $C_1$-$C_6$alkoxysilanes of the formula (S-I), $R_1R_2N$-L-Si(OR$_3$)$_a$(R$_4$)$_b$    (S-I), where
$R_1$, $R_2$ both represent a hydrogen atom, and
L represents a linear, bivalent $C_1$-$C_6$-alkylene group, preferably a propylene group (—CH$_2$—CH$_2$—CH$_2$—) or an ethylene group (—CH$_2$—CH$_2$—),
$R_3$ represents an ethyl group or a methyl group,
$R_4$ represents a methyl group or an ethyl group,
a stands for the number 3 and
b stands for the number 0.

Particularly well-suited organic silicon compounds of formula (I) are

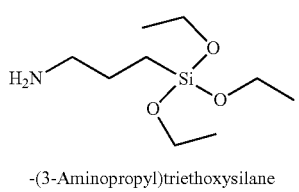

-(3-Aminopropyl)triethoxysilane

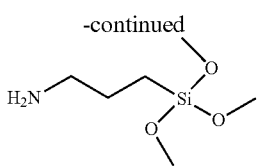

-(3-Aminopropyl)trimethoxysilane

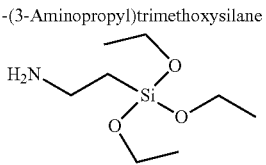

-(2-Aminoethyl)triethoxysilane

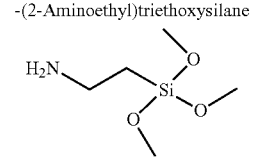

-(2-Aminoethyl)trimethoxysilane

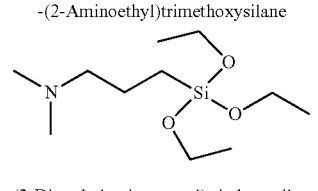

-(3-Dimethylaminopropyl)triethoxysilane

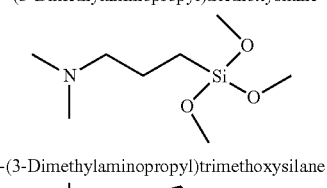

-(3-Dimethylaminopropyl)trimethoxysilane

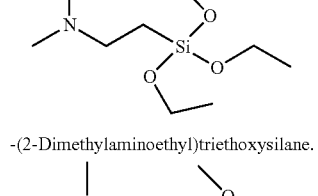

-(2-Dimethylaminoethyl)triethoxysilane.

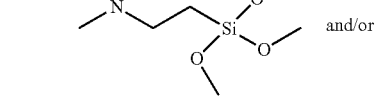 and/or

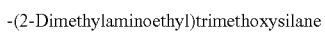

-(2-Dimethylaminoethyl)trimethoxysilane

In another preferred embodiment, a cosmetic agent comprises at least one organic $C_1$-$C_6$ alkoxysilane of the formula (S-I) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane,
(2-Dimethylaminoethyl)trimethoxysilane
and/or their condensation products.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In another embodiment, the cosmetic agent may also comprise one or more organic $C_1$-$C_6$ alkoxysilanes of formula (S-II),

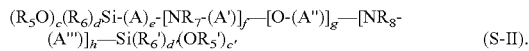                                                      (S-II).

The alkoxysilanes of the formula (S-II) carry at both ends the silicon-comprising groups $(R_5O)_c(R_6)_d Si$— and —$Si(R_6')_{d'}(OR_5')_{c'}$.

In the central part of the molecule of formula (S-II) there are the groups -$(A)_e$- and —$[NR_7$-$(A')]_f$- and —$[O$-$(A'')]_g$- and —$[NR_8$-$(A''')]_h$-. Here, each of the radicals e, f, g, and h can independently of one another stand for the number 0 or 1, with the proviso that at least one of the radicals e, f, g, and h is different from 0. In other words, a preferred alkoxysilane of formula (II) comprises at least one moiety selected from the group of -(A)- and —[NR$_7$-(A')]- and —[O-(A'')]- and —[NR$_8$-(A''')]-.

In the two terminal structural units $(R_5O)_c(R_6)_d Si$— and —$Si(R_6')_{d'}(OR_5')_{c'}$, the radicals R5, R5', R5" independently represent a $C_1$-$C_6$ alkyl group. The radicals R6, R6' and R6" independently represent a $C_1$-$C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing with the best wash fastness values could be obtained if the residues c and c' both stand for the number 3. In this case d and d' both stand for the number 0.

In another preferred embodiment, a cosmetic agent is wherein it comprises one or more organic $C_1$-$C_6$ alkoxysilanes of the formula (S-II),

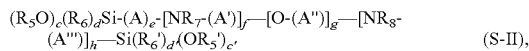                                                      (S-II), where
R5 and R5' independently represent a methyl group or an ethyl group,
c and c' both stand for the number 3 and
d and d' both stand for the number 0.

When c and c' are both 3 and d and d' are both 0, the organic silicon compounds as contemplated herein correspond to the formula (S-IIa)

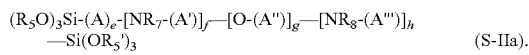                                                      (S-IIa).

The radicals e, f, g, and h can independently stand for the number 0 or 1, whereby at least one radical from e, f, g, h is different from zero. The abbreviations e, f, g, and h thus define which of the groupings -$(A)_e$- and —$[NR_7$-$(A')]_f$- and —$[O$-$(A'')]_g$- and —$[NR_8$-$(A''')]_h$- are in the middle part of the organic silicon compound of formula (II).

In this context, the presence of certain groupings has proven to be particularly advantageous in terms of achieving washfast dyeing results. Particularly satisfactory results could be obtained if at least two of the residues e, f, g, and h stand for the number 1. Especially preferred e and f both stand for the number 1. Furthermore, g and h both stand for the number 0.

When e and f are both 1 and g and h are both 0, the organic silicon compounds as contemplated herein are represented by the formula (S-IIb)

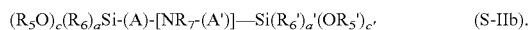                                                      (S-IIb).

The radicals A, A', A'', A''' and A'''' independently represent a linear or divalent, bivalent $C_1$-$C_{20}$ alkylene group. Preferably the radicals A, A', A'', A''' and A'''' independently of one another represent a linear, bivalent $C_1$-$C_{20}$ alkylene group. Further preferably the radicals A, A', A'', A''' and A'''' independently represent a linear bivalent $C_1$-$C_6$ alkylene group.

The divalent $C_1$-$C_{20}$ alkylene group may alternatively be referred to as a divalent or divalent $C_1$-$C_{20}$ alkylene group, by which is meant that each grouping A, A', A'', A''' and A'''' may form two bonds.

In particular, the radicals A, A', A'', A''' and A'''' independently of one another represent a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very preferably, the radicals A, A', A'', A''' and A'''' represent a propylene group (—$CH_2$—$CH_2$—$CH_2$—).

If the radical f represents the number 1, then the organic silicon compound of formula (II) as contemplated herein comprises a structural grouping —[NR$_7$-(A')]-. If the radical f represents the number 1, then the organic silicon compound of formula (II) as contemplated herein comprises a structural grouping —[NR$_8$-(A''')]-.

Wherein $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (S-III)

                                                      (S-III).

Very preferably the radicals R7 and R8 independently of one another represent a hydrogen atom, a methyl group, a 2-hydroxyethyl group, a 2-alkenyl group, a 2-aminoethyl group or a grouping of the formula (S-III).

When the radical f represents the number 1 and the radical h represents the number 0, the organic silicon compound as contemplated herein comprises the grouping [NR$_7$-(A')] but not the grouping —[NR$_8$-(A''')]. If the radical R7 now stands for a grouping of the formula (III), the organic silicon compound comprises 3 reactive silane groups.

In another preferred embodiment, a cosmetic agent comprises one or more organic $C_1$-$C_6$ alkoxysilanes of the formula (S-II)

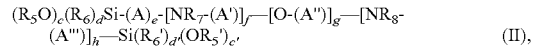                                                      (II), where
e and f both stand for the number 1,
g and h both stand for the number 0,
A and A' independently represent a linear, divalent $C_1$-$C_6$ alkylene group and
R7 represents a hydrogen atom, a methyl group, a 2-hydroxyethyl group, a 2-alkenyl group, a 2-aminoethyl group or a group of formula (S-III).

In a further preferred embodiment, the cosmetic agent comprises one or more organic $C_1$-$C_6$ alkoxysilanes of the formula (S-II), wherein
e and f both stand for the number 1,
g and h both stand for the number 0,
A and A' independently of one another represent a methylene group (—$CH_2$—), an ethylene group (—$CH_2$—$CH_2$—) or a propylene group (—$CH_2$—$CH_2$—$CH_2$—), and
R7 represents a hydrogen atom, a methyl group, a 2-hydroxyethyl group, a 2-alkenyl group, a 2-aminoethyl group or a group of formula (S-III).

Well-suited organic silicon compounds of the formula (S-II) are

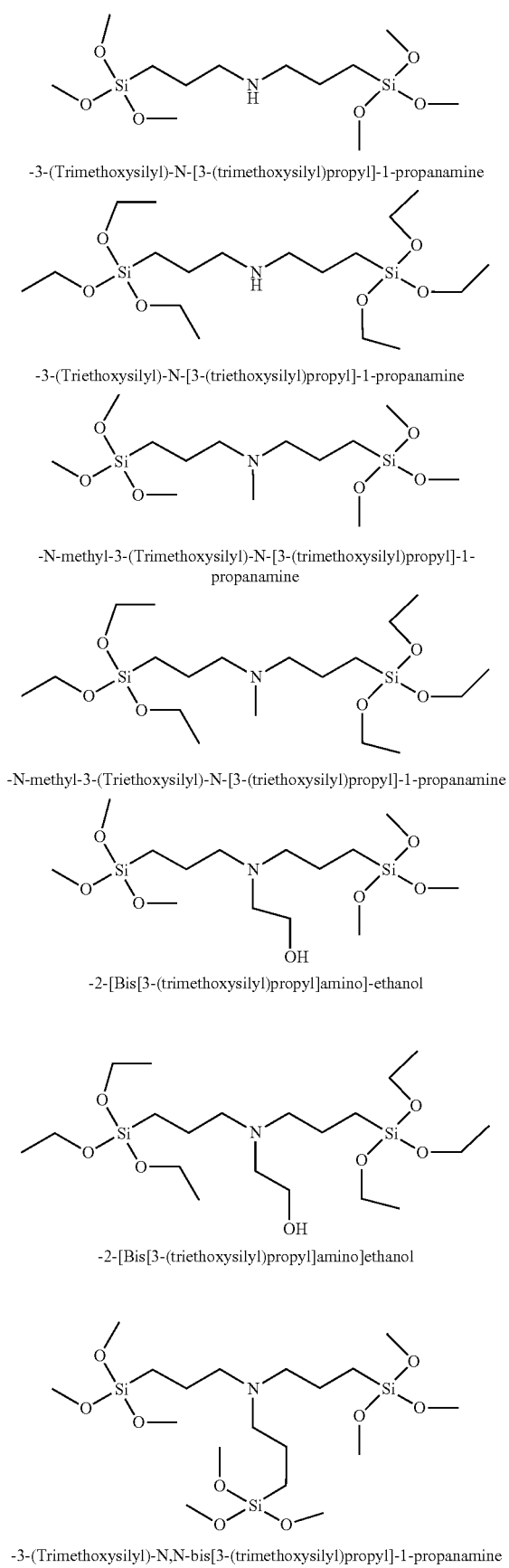
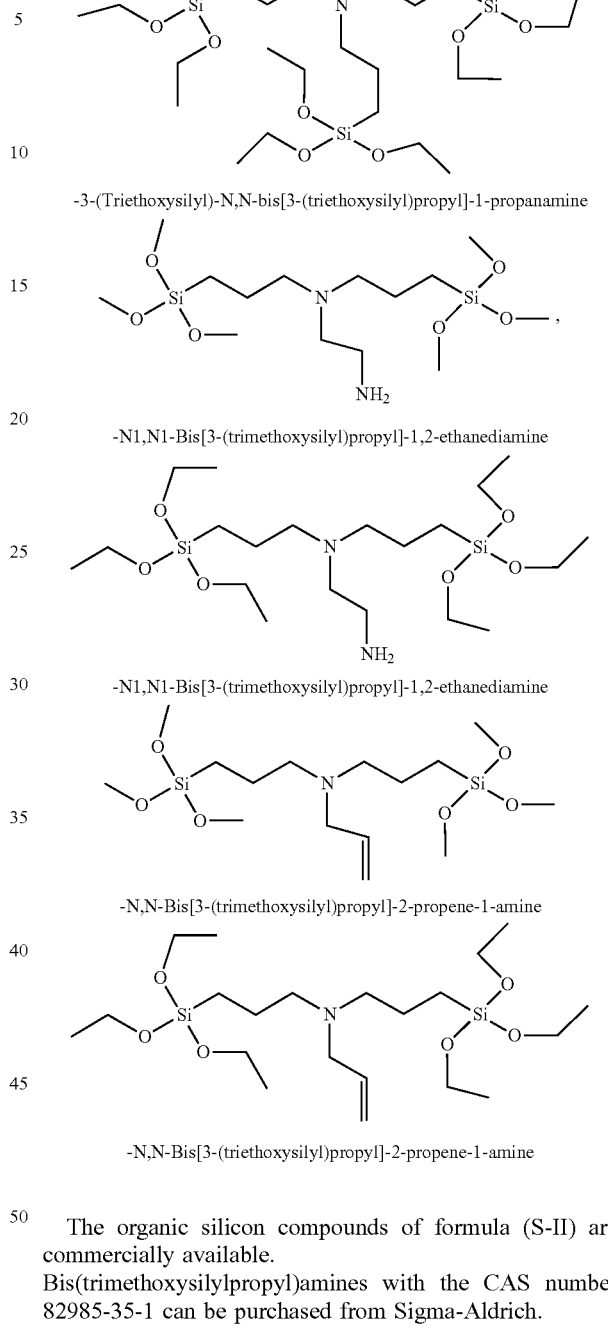

The organic silicon compounds of formula (S-II) are commercially available.

Bis(trimethoxysilylpropyl)amines with the CAS number 82985-35-1 can be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, a cosmetic agent comprises one or more organic $C_1$-$C_6$ alkoxysilanes of formula (S-II) selected from the group of 3-(Trimethoxysilyl)-N-[3-(trimethoxysilyl)propyl]-1-propanamine
3-(Triethoxysilyl)-N-[3-(triethoxysilyl)propyl]-1-propanamine
N-Methyl-3-(trimethoxysilyl)-N-[3-(trimethoxysilyl)propyl]-1-propanamine
N-Methyl-3-(triethoxysilyl)-N-[3-(triethoxysilyl) propyl]-1-propanamine
2-[Bis[3-(trimethoxysilyl)propyl]amino]-ethanol
2-[Bis[3-(triethoxysilyl)propyl]amino]ethanol
3-(Trimethoxysilyl)-N,N-bis[3-(trimethoxysilyl)propyl]-1-propanamine
3-(Triethoxysilyl)-N,N-bis[3-(triethoxysilyl)propyl]-1-propanamine
N1,N1-Bis[3-(trimethoxysilyl)propyl]-1,2-ethanediamine,
N1,N1-Bis[3-(triethoxysilylpropyl]-1,2-ethanediamine,
N,N-Bis[3-(trimethoxysilyl)propyl]-2-Propen-1-amine and/or
N,N-Bis[3-(triethoxysilyl)propyl]-2-propen-1-amine,
and/or their condensation products.

In dyeing tests, it has also been found to be particularly advantageous if the cosmetic agent comprises at least one organic $C_1$-$C_6$ alkoxysilane of the formula (S-IV)

$$R_9Si(OR_{10})_k(R_{11})_m \quad \text{(S-IV).}$$

The compounds of formula (S-IV) are organic silicon compounds selected from silanes having one, two or three silicon atoms, wherein the organic silicon compound comprises one or more hydrolysable groups per molecule.

The organic silicon compound(s) of formula (S-IV) may also be referred to as silanes of the alkyl-$C_1$-$C_6$ alkoxysilane type, $$R_9Si(OR_{10})_k(R_{11})_m \quad \text{(S-IV),}$$

where
$R_9$ represents a $C_1$-$C_{12}$ alkyl group,
$R_{10}$ represents a $C_1$-$C_6$ alkyl group,
$R_1$ represents a $C_1$-$C_6$ alkyl group
k is an integer from 1 to 3, and
m stands for the integer 3-k.

In a further embodiment, a particularly preferred cosmetic agent comprises one or more organic $C_1$-$C_6$ alkoxysilanes of the formula (S-IV), $$R_9Si(OR_{10})_k(R_{11})_m \quad \text{(S-IV),}$$

where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group
k is an integer from 1 to 3, and
m stands for the integer 3-k,
and/or their condensation products.

In the organic $C_1$-$C_6$ alkoxysilanes of formula (S-IV), the radical $R_9$ represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, $R_9$ stands for a methyl group, an ethyl group or an n-octyl group.

In the alkoxysilanes of formula (S-IV), the radical $R_{10}$ represents a $C_1$-$C_6$ alkyl group. Highly preferred $R_{10}$ stands for a methyl group or an ethyl group.

In the alkoxysilanes of formula (S-IV), the radical $R_{11}$ represents a $C_1$-$C_6$ alkyl group. Particularly preferably, $R_{11}$ represents a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Colorations with the best wash fastnesses could be obtained when the cosmetic agent comprises at least one organic $C_1$-$C_6$ alkoxysilane of formula (S-IV), in which the radical k represents the number 3. In this case the radical m stands for the number 0. Particularly suitable organic silicon compounds of the formula (S-IV) are

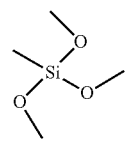

-Methyltrimethoxysilane

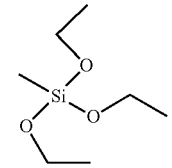

-Methyltriethoxysilane

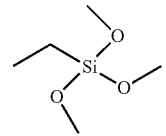

-Ethyltrimethoxysilane

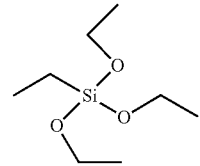

-Ethyltriethoxysilane

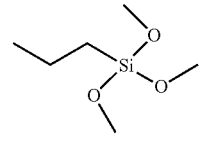

-n-Propyltrimethoxysilane (also known as propyltrimethoxysilane)

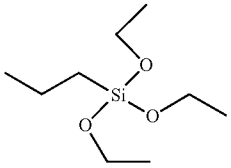

-n-Propyltriethoxysilane (also known as propyltriethoxysilane)

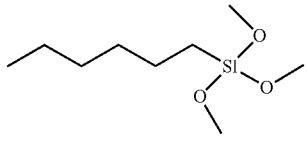

-n-Hexyltrimethoxysilane (also known as hexyltrimethoxysilane)

-continued

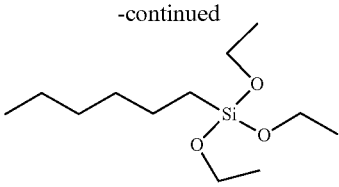
-n-Hexyltriethoxysilane (also known as hexyltriethoxysilane)

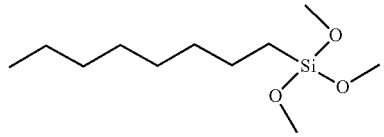
- n-Octyltrimethoxysilane (also known as octyltrimethoxysilane)

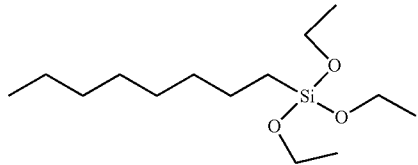
- n-Octyltriethoxysilane (also known as octyltriethoxysilane)

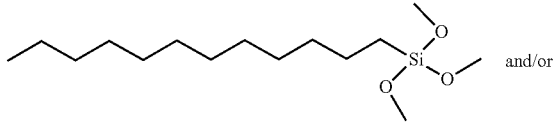 and/or
-n-Dodecyltrimethoxysilane (also known as dodecyltrimethoxysilane)

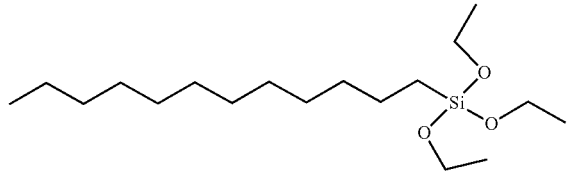
-n-Dodecyltriethoxysilanes (also known as dodecyltriethoxysilane)

and octadecyltrimethoxysilane and/or octadecyltriethoxysilane.

In another preferred embodiment, a cosmetic agent comprises at least one organic $C_1$-$C_6$ alkoxysilane of the formula (S-IV) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
Octadecyltrimethoxysilane,
Octadecyltriethoxysilane,
their mixtures
and/or their condensation products.

It has been found that regarding coloring keratinous material, it is particularly preferred if the cosmetic agent comprises two alkoxysilanes that are structurally different from each other.

In a preferred embodiment, a cosmetic agent comprises at least one alkoxysilane of the formula (S-I) and at least one alkoxysilane of the formula (S-IV).

The corresponding hydrolysis or condensation products are, for example, the following compounds:

Hydrolysis of $C_1$-$C_6$ alkoxysilane of formula (S-I) with water (reaction scheme using 3-aminopropyltriethoxysilane as an example):

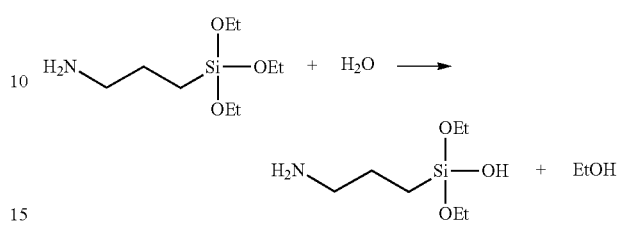

Depending on the amount of water used, the hydrolysis reaction can also take place several times per $C_1$-$C_6$ alkoxysilane used:

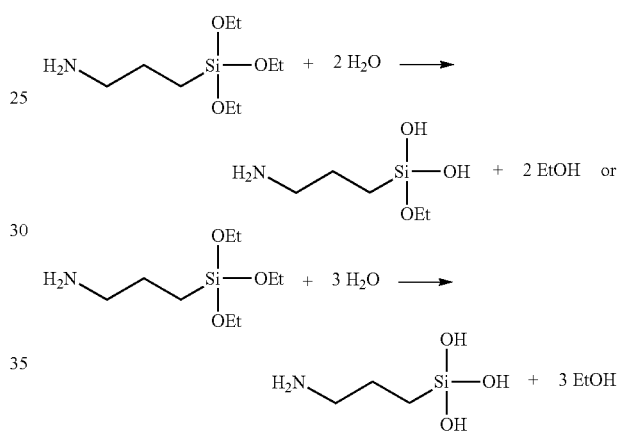

Hydrolysis of $C_1$-$C_6$ alkoxysilane of the formula (S-IV) with water (reaction scheme using methyltrimethoxysilane as an example):

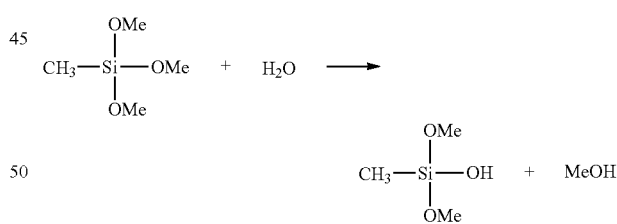

Depending on the amount of water used, the hydrolysis reaction can also take place several times per $C_1$-$C_6$ alkoxysilane used:

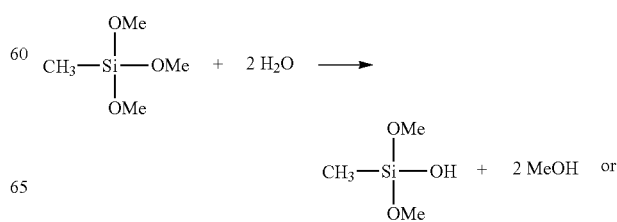

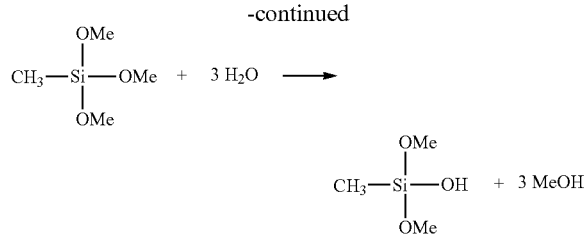

Condensation reactions include (shown using the mixture (3-aminopropyl)triethoxysilane and methyltrimethoxysilane):

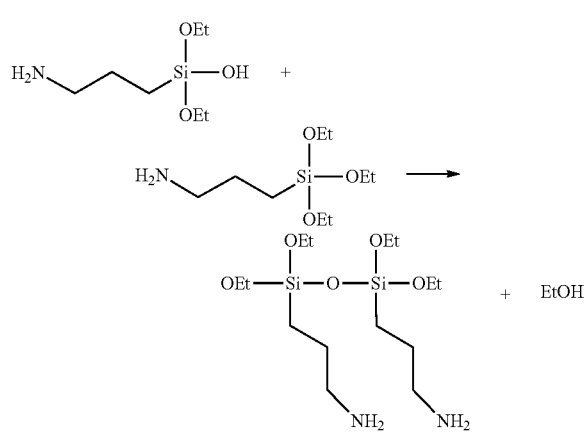

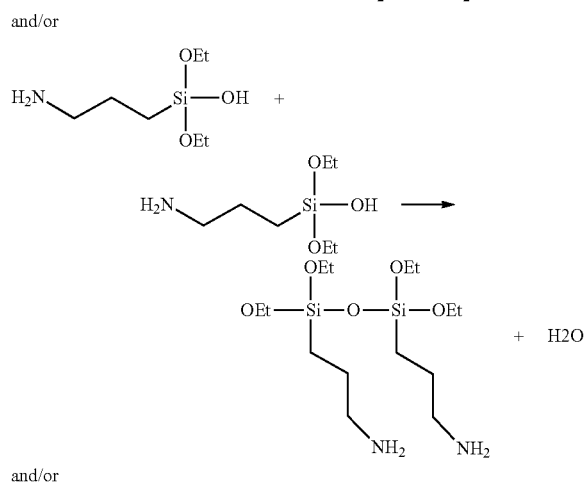

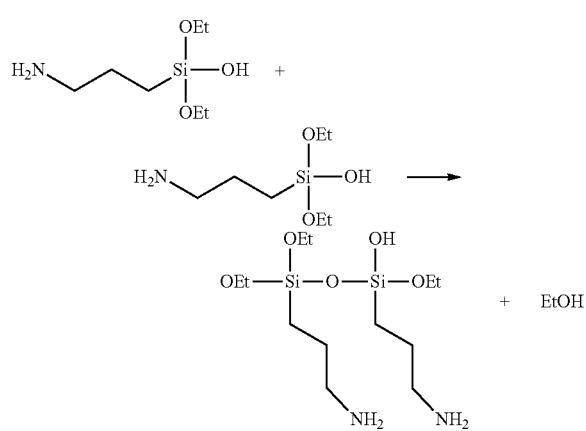

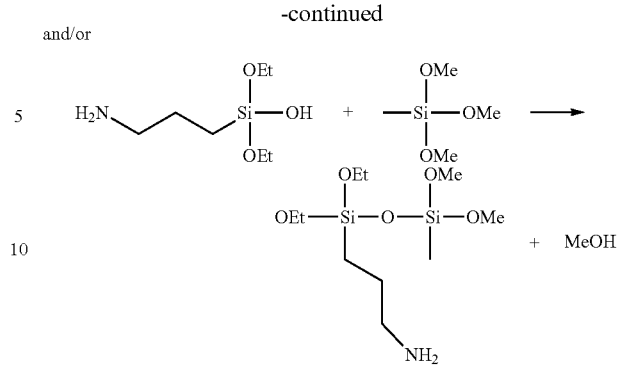

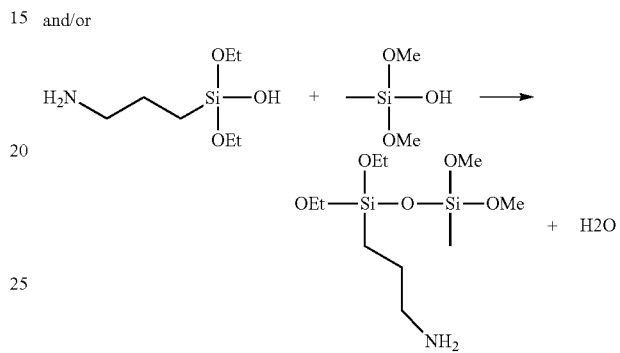

In the above exemplary reaction schemes the condensation to a dimer is shown in each case, but further condensations to oligomers with several silane atoms are also possible and preferred.

Both partially hydrolyzed and fully hydrolyzed $C_1$-$C_6$ alkoxysilanes of the formula (S-I) can participate in these condensation reactions, which undergo condensation with yet unreacted, partially, or also fully hydrolyzed $C_1$-$C_6$ alkoxysilanes of the formula (S-I). In this case, the $C_1$-$C_6$ alkoxysilanes of formula (S-I) react with themselves.

Furthermore, both partially hydrolyzed and fully hydrolyzed $C_1$-$C_6$-alkoxysilanes of the formula (S-I) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and fully hydrolyzed $C_1$-$C_6$-alkoxysilanes of the formula (S-IV) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-IV) react with themselves.

The cosmetic agent may contain one or more organic $C_1$-$C_6$ alkoxysilanes in various proportions. This is determined by the specialist depending on the desired application. In the case of coloring keratinous material, for example, the amount may depend on the thickness of the silane coating on the keratinous material and the amount of keratinous material to be treated.

Particularly storage-stable cosmetic agents with very good coloring results when applied to keratinous material could be obtained when the cosmetic agent comprises—based on its total weight—one or more organic $C_1$-$C_6$ alkoxysilanes and/or the condensation products thereof in a total amount of from 30 to 85 wt. %, preferably from 35 to 80 wt. %, more preferably from 40 to 75 wt. %, still more preferably from 45 to 70 wt. % and very particularly preferably from 50 to 65 wt. %.

It may be preferred that the cosmetic agent ready for use comprises further ingredients, in particular water, in addition to the pigment suspension as contemplated herein and the organic $C_1$-$C_6$ alkoxysilane(s).

The cosmetic agent comprises alkoxysilanes, a class of highly reactive compounds that can undergo hydrolysis or oligomerization and/or polymerization when applied.

To avoid premature oligomerization or polymerization, it may be of significant advantage to the user to prepare the ready-to-use cosmetic agent just prior to application.

A further advantage of the pigment suspension as contemplated herein is that it has no negative influence on the properties of the cosmetic agent and no negative influence on the properties of the organic $C_1$-$C_6$ alkoxysilanes.

To increase user convenience, the user is preferably provided with all the necessary agents in the form of a multi-component packaging unit (kit-of-parts).

Thus, a third object of the present disclosure is a multi-component packaging unit (kit-of-parts) comprising, separately assembled from each other a first container comprising an agent (a'), wherein the agent comprises (a'): (a1) at least one or more organic $C_1$-$C_6$-alkoxysilanes, and a second container comprising an agent (a"), wherein the agent comprises (a"): (a2) a pigment suspension as contemplated herein.

In this embodiment, the cosmetic agent is prepared by mixing the agent (a') and the agent (a"). Regarding further preferred embodiments of the cosmetic agent and/or the multi-component packaging unit (kit-of-parts), the same applies mutatis mutandis as to the pigment suspensions.

Examples

1. Pigment Suspension

To prepare a pigment suspension as contemplated herein, 10 g iron oxide red pigments (CI 77491) with an average particle diameter in the range of 2,000 to 4,000 nm were mixed with 10 g ceteth-20 phosphates (INCI) and 80 g distilled water. The mixture was transferred to a ball mill and the iron oxide red pigments were crushed.

After completion of the milling process, the particle size of the iron oxide red pigments was in the range of 150 to 700 nm. How was the particle size determined?

The pigment suspension obtained was stable over several weeks and the iron oxide red pigments showed no tendency to agglomerate.

For comparison, a pigment suspension was prepared from 10 g iron oxide red pigments (CI 77491) with an average particle diameter in the range of 2,000 to 4,000 nm and 90 g PEG-12 dimethicone (INCI) and subjected to a grinding process in a ball mill.

After completion of the milling process, the particle size of the iron oxide red pigments was in the range of 150 to 700 nm, but the iron oxide red pigments agglomerated shortly after completion of the milling process.

2. Hair Dye

The following formulations have been produced (unless otherwise indicated, all figures are in wt. %)

| Agent (a') | |
| --- | --- |
| | wt.-% |
| (3-Aminopropyl)triethoxysilane | 24 |
| Methyltriethoxysilane | 72 |
| Water | ad 100 |

| Agent (a") (=pigment suspension) | |
| --- | --- |
| | wt. % |
| Iron oxide red (CI 77491, ⁻ = 150-700 nm) | 10 |
| Ceteth-20 Phosphate (INCI) | 10 |
| Water | ad 100 |

The cosmetic agent was prepared by mixing 5 g of agent (a') and 5 g of agent (a").

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A pigment suspension comprising
    a) at least one coloring compound selected from the group consisting of pigments,
    b) at least one phosphoric ester comprising an ester of orthophosphoric acid with an aliphatic alcohol, and
    c) water.

2. The pigment suspension of claim 1, wherein the coloring compound comprises a pigment selected from the group of iron oxide pigments.

3. The pigment suspension of claim 2, wherein the iron oxide pigment is selected from the group consisting of black iron oxide (CI 77499), yellow iron oxide (CI 77492), red iron oxide (CI 77491), and mixtures thereof.

4. The pigment suspension of claim 1, wherein at least one coloring compound has a particle diameter of from 100 to 1,000 nm.

5. The pigment suspension of claim 1, wherein the at least one coloring compound comprises an organic pigment.

6. The pigment suspension of claim 1, wherein the at least one coloring compound comprises at least one organic pigment selected from the group consisting of carmine, quinacridone, phthalocyanine, Sorgho, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with the color index numbers CI 61565, CI 61570, CI 74260, orange pigments with the color index numbers CI 11725, CI 15510, CI 45370, CI 71105, red pigments with the color index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470, and mixtures thereof.

7. The pigment suspension of claim 1, wherein the at least one coloring compound has a particle diameter of from 150 to 700 nm.

8. The pigment suspension of claim 1, wherein the at least one phosphoric acid ester comprises an ester of orthophosphoric acid with a branched aliphatic alcohol having 11 to 14 carbon atoms.

9. The pigment suspension of claim 1, wherein the at least one phosphoric acid ester comprises an ester of orthophosphoric acid with an ethoxylated aliphatic alcohol having 8 to 18 carbon atoms.

10. The pigment suspension of claim 1, wherein the at least one phosphoric acid ester comprises an ester having the INCI designation Ceteth-20 phosphates.

11. A cosmetic agent obtainable by combining a pigment suspension comprising (a) at least one coloring compound selected from the group consisting of pigments, (b) at least one phosphoric ester, wherein the at least one phosphoric ester comprises an ester of orthophosphoric acid with an aliphatic alcohol, and (c) water, with one or more organic $C_1$-$C_6$ alkoxysilanes and/or condensation products thereof.

12. The cosmetic agent of claim 11, wherein the cosmetic agent comprises one or more organic $C_1$-$C_6$ alkoxysilanes of the formula (S-I) and/or (S-II) and/or (S-IV),

  (S-I)

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a, stands for an integer from 1 to 3, and
b stands for the integer 3-a, and

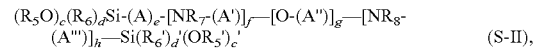  (S-II), where
R5, R5', R5", R6, R6' and R6" independently represent a $C_1$-$C_6$ alkyl group,
A, A', A", A''' and A'''' independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III),

  (S-III), where
c stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g, and h radicals are different from 0,
and/or

  (S-IV), where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group
k is an integer from 1 to 3, and
m stands for the integer 3-k.

13. The cosmetic agent of claim 11, wherein the cosmetic agent comprises at least two structurally different organic $C_1$-$C_6$ alkoxysilanes.

14. A kit-of-parts for dyeing keratinous material, comprising separately packaged
a first container comprising an agent (a') comprising:
(a1) at least one or more organic $C_1$-$C_6$-alkoxysilanes, and
a second container comprising an agent (a") comprising:
(a2) a pigment suspension comprising (a) at least one coloring compound selected from the group consisting of pigments, (b) at least one phosphoric ester, and (c) water, wherein the at least one phosphoric ester a comprises an ester of orthophosphoric acid with an aliphatic alcohol.

* * * * *